United States Patent [19]

Gaffar

[11] Patent Number: 5,234,688

[45] Date of Patent: * Aug. 10, 1993

[54] ANTI-PLAQUE DENTIFRICE PACKAGED IN RESILIENT SQUEEZABLE FORM MAINTAINING DISPENSING CONTAINER

[75] Inventor: Abdul Gaffar, Princeton, N.J.

[73] Assignee: Colgate-Palmolive Company, Piscataway, N.J.

[*] Notice: The portion of the term of this patent subsequent to Aug. 4, 2009 has been disclaimed.

[21] Appl. No.: 547,642

[22] Filed: Jul. 2, 1990

Related U.S. Application Data

[63] Continuation-in-part of Ser. No. 505,628, Apr. 6, 1990, Pat. No. 5,167,951, and Ser. No. 427,660, Oct. 26, 1989, Pat. No. 5,135,738, Ser. No. 410,682, Sep. 21, 1989, abandoned, Ser. No. 398,566, Aug. 25, 1989, Pat. No. 5,032,386, Ser. No. 398,605, Aug. 25, 1989, abandoned, Ser. No. 398,606, Aug. 25, 1989, abandoned, Ser. No. 399,669, Aug. 25, 1989, abandoned, Ser. No. 398,592, Aug. 25, 1989, Pat. No. 5,188,821, and Ser. No. 291,712, Dec. 29, 1988, Pat. No. 4,894,220.

[51] Int. Cl.$^5$ .................. A45D 40/00; A61K 7/16; A61K 7/18; A61K 7/26
[52] U.S. Cl. ...................... 424/401; 424/49; 424/52; 424/126; 424/58; 514/970; 206/524.1; 206/524.4; 206/524.5; 222/105
[58] Field of Search .................. 424/49–58, 424/126, 401; 514/970; 206/524.1, 524.4, 524.5; 222/105

[56] References Cited

U.S. PATENT DOCUMENTS

| | | | |
|---|---|---|---|
| 4,830,221 | 5/1989 | Mazzanobile | 424/49 |
| 4,933,171 | 6/1990 | Bristow et al. | 424/49 |
| 4,933,173 | 6/1990 | Bristow et al. | 424/49 |
| 4,980,153 | 12/1990 | Jackson et al. | 424/49 |
| 4,988,499 | 1/1991 | Bristow et al. | 424/52 |
| 5,019,373 | 5/1991 | Carter et al. | 424/49 |
| 5,026,539 | 6/1991 | Jackson et al. | 424/49 |
| 5,032,385 | 7/1991 | Reed et al. | 424/49 |
| 5,135,738 | 8/1992 | Gaffar et al. | 424/49 |

*Primary Examiner*—Shep K. Rose
*Attorney, Agent, or Firm*—Robert L. Stone; Murray M. Grill; Robert C. Sullivan

[57] ABSTRACT

A dental composition, such as a paste or gel dentifrice containing triclosan, as an antibacterial agent which acts to decrease plaque on the teeth, is packaged in a hand holdable and squeezable dispensing container which is made of or includes a part or parts of a solid polymeric material, such as a polyfluoroethylene or polyvinyl chloride, which is compatible with triclosan, so that excessive loss of its anti-plaque activity on storage is avoided, which losses have been noted when various other plastics have been employed as dispensing container component materials. Alternatively, other more reactive plastics may be employed for such dispensing container parts when a stabilizer, such as terpene, e.g., limonene, is present in the dentifrice. The dentifrice preferably also contains an anti-tartar proportion of polyphosphate, a tooth hardening proportion of a source of fluoride ions, a stabilizing proportion (in conjunction with the fluoride source) for the polyphosphate, of a polyvinyl methyl ether/maleic anhydride copolymer, and normal dentifrice components and adjuvants.

27 Claims, 2 Drawing Sheets

ANTI-PLAQUE DENTIFRICE PACKAGED IN RESILIENT SQUEEZABLE FORM MAINTAINING DISPENSING CONTAINER

This application is a continuation-in-part of U.S. patent application Ser. No. 07/505,628, filed Apr. 6, 1990, and now U.S. Pat. No. 5,167,951, granted Dec. 1, 1992, U.S. patent application Ser. No. 07/427,660, filed Oct. 26, 1989, now U.S. Pat. No. 5,135,738, granted Aug. 4, 1992, U.S. patent application Ser. No. 07/410,682, filed Sep. 21, 1989, U.S. patent application Ser. No. 07/398,566, now U.S. Pat. No. 5,032,386, granted Jul. 16, 1991; 07/398,605; 07/398,606 and 07/399,669, each not abandoned, all of which were filed on Aug. 25, 1989, Ser. No. 07/398,592, filed Aug. 28, 1989, now U.S. pat. No. 5,188,821 and U.S. patent application Ser. No. 07/291,712, filed Dec. 29, 1988 and now U.S. Pat. No. 4,894,220 granted Jan. 16, 1990.

This invention relates to packaged anti-plaque dental compositions which comprises an antibacterial agent, triclosan (THDE, 2',4,4'-trichloro-2-hydroxydiphenylether), as an effective anti-plaque component, which compositions are packaged in a squeezable dispensing container which includes a polymeric plastic material in contact with the dental composition, which plastic is compatible with the triclosan in the composition.

Although various plastics may diminish the anti-plaque action of triclosan, certain plastics, such as polyfluoroethylene and polyvinyl chloride, have been found to be compatible with triclosan dentifrices and it has been discovered that they do not cause excessive losses of antibacterial and anti-plaque activities of such dentifrices contacting them during storage at room temperature, and even at elevated temperatures. Also, applicant has discovered that when parts of the container that contact the dentifrice are of a plastic which is not in itself entirely compatible with triclosan, compatibility can be improved by incorporating in the dentifrice formula a stabilizing proportion of a material discovered by applicant to have stabilizing properties, such as a terpene, e.g., limonene, or an essential oil (natural or synthetic), which may be a component of a flavoring material for the dentifrice, and thereby can perform a dual function in the packaged dentifrice. When the packaged dentifrice is in contact with a plastic that could otherwise inhibit the antibacterial and anti-plaque action of the triclosan such stabilizer will be present in sufficient proportion so that the dentifrice, as packaged and dispensed, is effective in anti-plaque action, which is a major object of this invention.

The packaged dentifrices of the invention preferably include in the dentifrice compositions an anti-tartar proportion of polyphosphate, fluoride or a source of fluorine ions for tooth hardening and anti-caries actions, and polyvinyl methyl ether/maleic anhydride copolymer, which, in conjunction with the fluoride, stabilizes the polyphosphate anti-tartar agent and improves the anti-plaque action of triclosan.

Plaque on teeth is considered to be a causative factor of negative periodontal conditions, and dental plaque is a precursor of calculi. Plaque may form on any part of the tooth surface, including the gingival margin. It makes the teeth appear dull and in addition to promoting development of calculi, it has been implicated in occurrences of gingivitis. Therefore, dentifrices that contain anti-plaque components, which prevent or inhibit the development of plaque on the teeth, are valuable dental care aids. Tartar or dental calculus, is also known to be causative of gingivitis and dental decay, and makes the teeth appear dull and unattractive. Although it has been known that antimicrobial agents in dentifrices may reduce plaque, various other antibacterial compounds than triclosan and the like are often of disadvantageous characteristics which contrindicate their employment in such oral compositions. For example, cationic antibacterial compounds, such as quaternary ammonium halides, tend to discolor the teeth and may be inactivated by the presence of anionic materials in the oral preparations (and often it will be desirable to employ anionic surfactants or detergents in such oral compositions). Triclosan can be inactivated by nonionic surfactants and by various plastics, as has been discovered by applicant. Thus, an object of this invention has been to incorporate triclosan, and similar compounds, such as DDDE (2,2'-dihydroxy-5,5'-dibromo-diphenyl ether), in dental compositions for their anti-plaque activity and to store such compositions and dispense them from packages or containers in which they will not lose an excessive proportion of such activity on storage, before intended use, or during dispensing. In prior art triclosan dentifrices, as delivered from the dispenser, the triclosan delivery has not been in an effective amount to significantly reduce plaque when employed once or twice daily at 1.5 grams of dentifrice for one minute brushings, which is considered to approximate normal brushing practice. To be effective, such uses should result in at least a 25% reduction in plaque after three weeks' use, compared to similar usage of a control toothpaste Triclosan is described in U.S. Pat. No. 4,002,880 as an antibacterial agent in combination with an anti-calculus agent (which provides zinc ions), and it is disclosed in German patent specification (OLS) No. 35,32 860 in combination with a copper compound. It is also mentioned in European patent applications No's. 0 161 898 and 0 161 899, and in European patent application No. 0 220 890 it is disclosed in dentifrices with polyethylene glycol and oil based flavor.

Various types of dentifrices are known, including paste, gel, powder, liquid, tablet, lozenge, sachet and packeted dentifrices. Such products have been packed in deformable or squeezable tubes, pressurized dispensers, packets, bottles, jars, pump dispensers and other containers. In recent years some such containers have been made of synthetic organic polymeric plastics or of laminates which include such plastics. Interactions between dentifrices and the materials of containers in which they were packed have been known, such as reactions between toothpastes and aluminum containers, and to prevent such reactions containers have been especially treated or different container materials have been employed. However, applicant does not believe that before their invention it had been known to the prior art that plastic dispenser materials of construction could adversely affect the anti-plaque activities of triclosan (and DDDE and similar anti-plaque agents) that had been included in contained dentifrices, in which they came into contact with such plastics, nor does he believe that it had been discovered that certain plastics could be employed for such container parts without causing losses of the anti-plaque activities of triclosan and related halogenated diphenyl ethers (triclosan only will be referred to later herein, for simplicity) or that losses of such anti-plaque activity of dentifrices packed in dispensers in contact with "reactive" plastics (which react with, absorb or otherwise reduce the anti-plaque actions of the dentifrices) could be inhibited or prevented by incorporation in the dentifrices of terpenes, such as limonene, and other stabilizing components of flavoring materials.

Polyphosphates, which are anti-tartar compounds of the preferred packaged dentifrices, tooth hardening and stabilizing fluoride or other source of fluorine ions, and polymeric polycarboxylate, such as the polyvinyl methyl ether/maleic anhydride copolymers, which can increase the effectivenesses of the polyphosphate and fluoride, and act to inhibit development of calculi, are dental preparation components that are known to the art. U.S. patent application Ser. No. 07/398,772, filed Aug. 25, 1989, U.S. Pat. Nos. 4,323,551, 4,515,772 and 4,627,977, and European patent application 89 200 710.5 are considered to be of relevance to such aspects of the present invention.

Squeezable and form maintaining resilient dispensing containers for viscous materials, which are the preferred dispensing containers for dentifrices in accordance with the present invention, are described in U.S. Pat. No. 4,842,165. The dispenser illustrated in that patent is of suitable tubular shape, vertically storable, resilient, lined with a flexible bag, and is equipped wit check valve means to promote easy and complete dispensings.

In accordance with the present invention a resilient squeezable dispensing container of a viscous anti-plaque dentifrice comprises such a dentifrice, which comprises an effective anti-plaque proportion of triclosan, in a resilient squeezable dispensing container which has a walled dispensing chamber, in which container parts thereof that contact the dentifrice during storage and during dispensing thereof are of material(s) that is/are compatible with the triclosan in the dentifrice and do(es) not cause excessive loss(es) of anti-plaque properties of the dentifrice during storage thereof in and dispensing thereof from the squeezable dispensing container. The losses of anti-plaque activity are desirably held by the present invention to less than 25% on aging at room temperature and at elevated temperature, e.g., three weeks at 40° C., and such activity will preferably be maintained at such a level for at least a year at room temperature. Such stabilization of the triclosan (which is evidence by such limited losses of anti-plaque activity) is effected by employing in the dispenser parts that are compatible with the triclosan, such being of polyfluorocarbons, preferably of the polyfluoroethylene type, e.g., polytetrafluoroethylene, or polyvinyl compounds, preferably polyvinyl halides, e.g., polyvinyl chloride. However, an alternative technique is to include a stabilizing material in the dentifrice, which material may be a terpene, e.g., limonene, or a flavor incorporating such a terpene or other stabilizer. Such stabilizing action may be inhibition of chemical reactions of the triclosan with the plastic or with other materials in the presence of the plastic, may be inhibition of sorption of the triclosan by the plastic, or may be another mechanism, unknown at the present. For example, the terpenes may react with the plastics or components of the plastics and thereby prevent reactions thereof with the triclosan. The described dentifrices preferably also include the previously mentioned polyphosphates, fluorides, and copolymers in such proportions as to be effective for their desired functions.

The invention will be readily understood from the description thereof in this specification, taken in conjunction with the drawing, in which.

Figure 1:
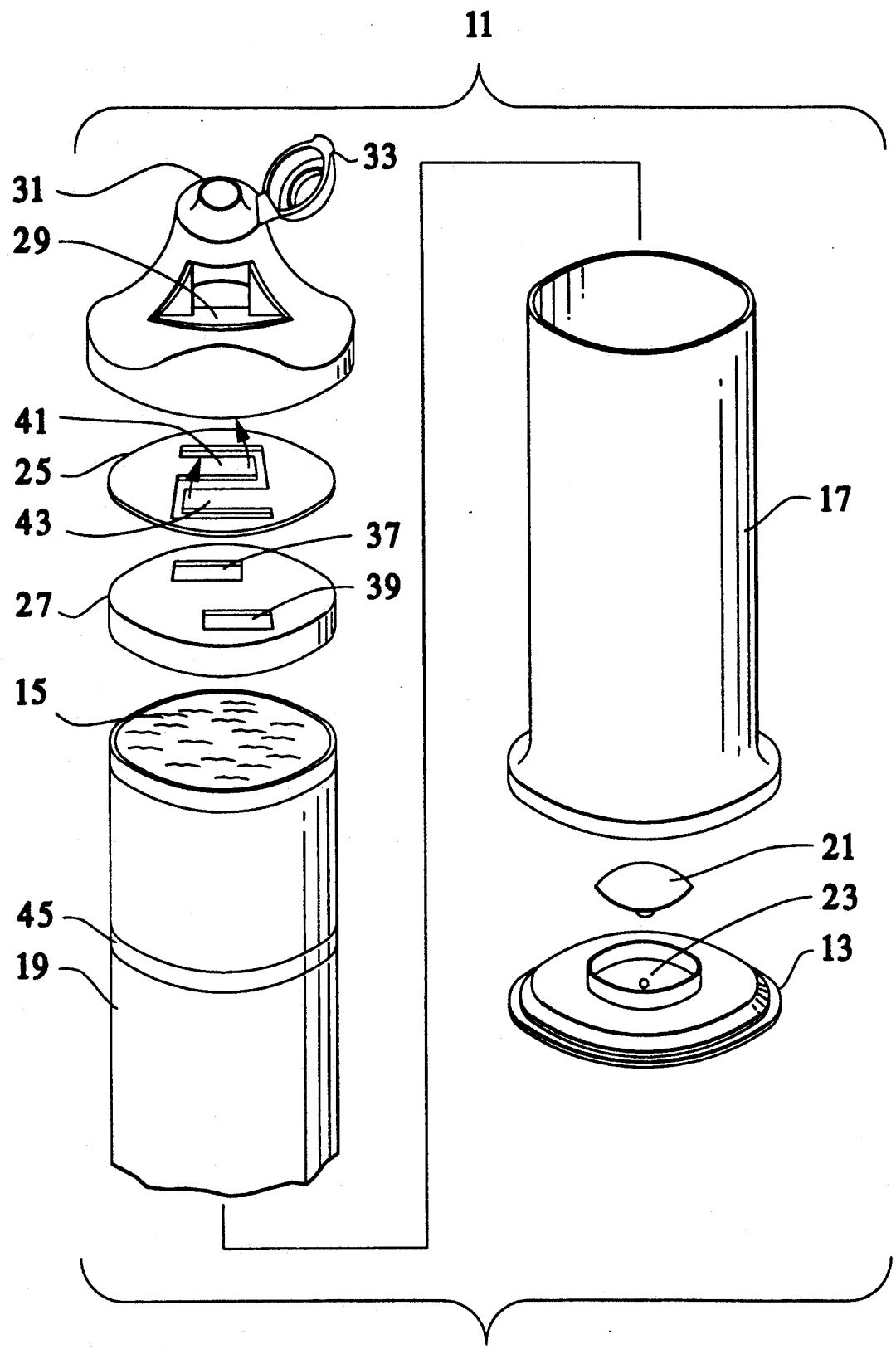
FIG. 1 is a disassembled elevational view of a preferred dispensing container of the invention, containing dentifrice ready to be dispensed.
Figures 2, 3:
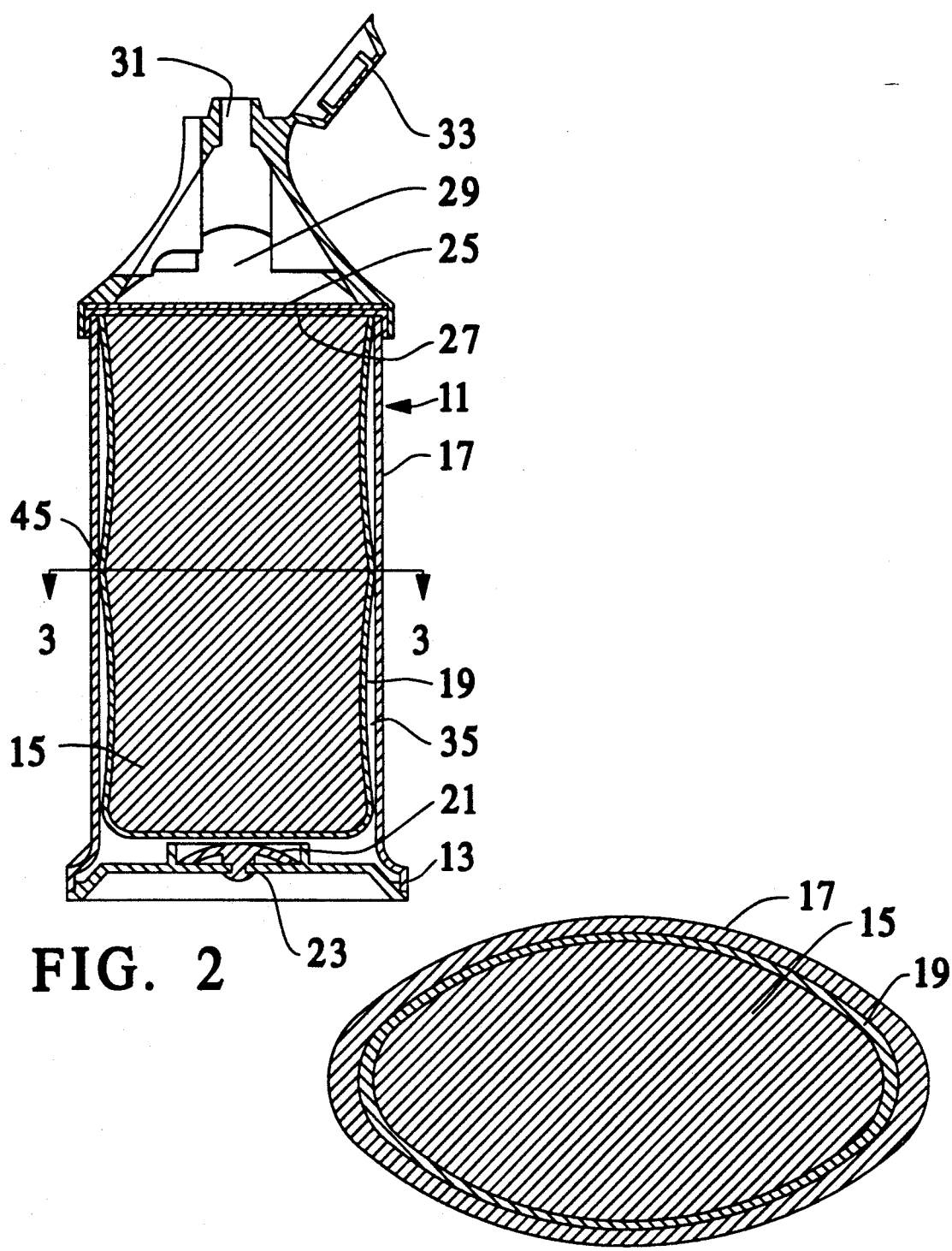
FIG. 2 is a vertical sectional elevational view of the assembled package of FIG. 1.
FIG. 3 is a horizontal sectional view of the package along plane 3—3 of FIG. 2.

In FIG. 1 there is illustrated a squeezable resilient dispenser of the type described in U.S. Pat. No. 4,842,165, which may be referred to as the squeeze dispenser. Dispensing container 11, containing dentifrice 15, includes a base 13, walled resilient elliptical or cylindrical tube 17, bag or liner 19, air check valve parts 21 and 23, suckback limiting parts 25 and 27, walled dispensing passageway 29, outlet, nozzle or orifice 31 and hinged cap 33.

The tubular container body 17, bottom 13, air check valve parts 21 and 23 and other parts of the dispensing container that do not come into contact with the contained dentifrice, during storage or discharge thereof, may be of any suitable material, such as synthetic organic polymer of the type normally referred to as "plastic". However, it is desirable that all parts that are in contact with the dentifrice, especially those parts which are in contact therewith during lengthy storage, should be of a material which does not adversely affect the triclosan component of the dentifrice (and other components thereof, for that matter). Thus, it is especially important that the bag or liner 19 be of a material which does not substantially adversely affect the triclosan and it is desirable that the passageway 29, orifice 31, suckback limiting parts 25 and 27 and cap 33 should be of non-reactive plastic, but if the materials of construction of any such parts are such as tend to react with triclosan or otherwise adversely affect its anti-plaque activity in the dentifrice composition, the dentifrice formula should contain a stabilizing material, such as a terpene, e.g., limonene.

Among the highly preferred polymers which are substantially non-reactive with triclosan in the present dentifrices are polyfluorocarbons, such as polytetrafluoroethylene, and polyvinyl halides, such as polyvinyl chloride. Also non-reactive, although their physical properties may militate against their use for some parts of the dispensing container, are polycarbonates and polysulfones. Sometimes it will be desirable for the parts to be made entirely of one of such materials or of laminates or of other combinations thereof but often certain required physical properties and/or economics may favor employment of a different polymer, even such a polymer as may be objectionably reactive with triclosan. Among such polymers there may be mentioned poly-lower alkylenes, such as polyethylene (both low density and high density) and polypropylene, polyethers, polyesters, such as polyethylene terephthalate, nylons, polyacrylates, polyallomers and polymethyl pentenes. Such materials are employable in contact with the dentifrice if a suitable stabilizer is present in the dentifrice composition. For such materials to be useful as materials of construction for the flexible bags of the present dispensers they will normally have to be flexible enough and capable of being made thin enough so as to be turnable inside-out as dentifrice is dispensed, so as to force substantially all the dentifrice out of the dispensing container. Normally such materials will be in thin sheet or film form but sometimes they may be applied as melts or solvent solutions in thin coatings onto other films or sheet materials. The total thickness of such a bag or laminate of such material(s) will normally be in the range of 0.001 to 0.005 inch, or 0.02 to 0.1 mm. In a desirable embodiment of the invention the laminate may be of 0.02 mm. thick polyethylene, 0.01 mm. thick polyethylene terephthalate, 0.002 mm. thick aluminum and 0.02 mm. polyethylene, reading from inside to outside. The squeezable resilient outer body portion of the dispensing container may be of any suitable resilient material, such as polyethylene or polyvinyl chloride, with the main requirement for it being that it should be resilient enough to return to initial position immediately after release of squeezing forces thereon.

In operation, upon squeezing of tube 17 (after removal of cap 33) air check valve part 21 closes the opening in part 23, thereby preventing escape of air from any clearance 35 between the inner portion of tube 17 and the outer surface of bag 19. Then, squeezing forces and the internal air pressure built up force viscous dentifrice 15 through openings 37 and 39 of suckback limiting part 27 and past flaps 41 and 43 of part 25, through passageway 29 and out through orifice 31. Upon release of squeezing pressure the valve part 21 moves away from part 23, allowing entry of air into the container, and flaps 41 and 43 close off openings 37 and 39 and thereby prevent excessive sucking back into the bag or liner, of dentifrice, and of an equal volume of air into the discharge passageway. Because of the limiting of the sucking back of material upon the release of squeezing forces, undesirable air "belching" on the next dispensing is avoided.

Essentially complete discharge of the viscous dentifrice from the bag or liner is obtainable because the bag or liner is turned "inside-out" during dispensing due to the fact that it is held at its circumference, along a band 45, to the interior of tube 17 by suitable means, such as cementing or fusing. However, some material will be left in the discharge passageway and this too can be discharged by finger pressure on the exterior of such passageway material providing that such material is flattenable by such finger pressure.

In the description of the invented package of FIG.'s. 1-3 the terms "upwardly" and "downwardly" are used in a relative sense only and it will be apparent to the reader of this specification that dispensings of the package's contents may be effected while the container is held in various orientations, including inverted positions.

The various internal parts of the resilient squeezable dispensers that contact the dentifrice are preferably of plastic(s) that do not inactivate triclosan but if it is not feasible to utilize plastics that have the necessary physical properties for the various contacting parts and still are compatible with triclosan other plastics may be employed, preferably such as adversely affect triclosan less than do other plastics, and more preferably, only slightly. Such dentifrices preferably include a stabilizing substance, such as limonene or other stabilizing terpene or flavor component. However, it is considered best, if feasible, to avoid employing any co-polyester/polyether elastomers, such as have sometimes in the past been used for internal membranes or liners, which plastic appears to be especially detrimental to triclosan stability in dentifrices.

Because triclosan is to some extent photosensitive, it will sometimes be desirable for the resilient squeezable dispensers of this invention to include containers, closures and caps which are coated or laminated with a chemical or physical light screening material, many of which materials are known, to prevent transmissition to the dentifrice and to the triclosan therein of any inactivating radiation, e.g., ultraviolet light. Also, such containers may desirably be opaque to prevent such actinic radiation from inactivating the triclosan in the dentifrice.

The cause(s) of inactivation by plastics of triclosan's anti-plaque action in packaged dentifrices has/have not yet been established. Research to date has not pinpointed the mechanism responsible for losses of such desirable activity and so far test results do not conclusively point either to chemical reactions or to physical absorptions. Tests of some oral preparations containing triclosan show that when they are aged in dispensing containers at room temperature, 38° C. and 49° C., for up to twelve weeks, there can be "excessive" losses (over 25% of the effect of the initial concentration of triclosan being lost) when such a preparation has been in contact with such container walls and parts of low density polyethylenes, high density polyethylenes, polyethylene terephthalates, polypropylenes, nylons, polyallomers and polymethylpentenes. Similarly, high losses result when such storage is in containers with inner walls or parts of co-polyester/polyether elastomers, such as those which had previously been employed in membranes for dispensing containers. In other experiments it was found that polyfluorocarbons and polyfluoroethylenes, such as polytetrafluoroethylenes, polyvinyl chlorides, polycarbonates and polysulfones, did not absorb or react with excessive proportions of triclosan. However, polycarbonates and polysulfones are brittle and hence can be unsuitable for employment for some dispensing container parts. Polyvinyl chlorides can sometimes impart a foreign taste to dentifrices, and therefore might be avoided as a packaging material, except in cases where such taste is compatible with the taste of the flavoring employed. Thus, of all the polymeric plastic materials available, polyfluorocarbons or polyfluoroethylenes are especially satisfactory materials for use in the present containers or packages, and do not seriouly diminish the anti-plaque activity of triclosan. However, as was indicated previously, by incorporation in the oral compositions of suitable stabilizing compounds for triclosan, such as terpenes, of which limonene is representative, essential oils (which often contain terpenes) and other flavor components with similar "stabilizing" properties, one is able to reduce the activity losses of the triclosan when dentifrices containing it are in contact with containers or container parts made of the various mentioned polymeric plastics which are "stabilizable", so that excessive losses in anti-plaque activity do not occur. Therefore, one need not be dependent on polyfluoroethylene as a dispenser material, providing that the dentifrice also contains a stabilizing proportion of terpene or other suitable "stabilizer". When such stabilizer is present in the oral compositions or when polyfluoroethylene (or polyvinyl chloride, polycarbonate polysulfone or any combination thereof is/are the only polymeric plastic(s) in contact with the oral composition, storage losses of anti-plaque activity are less than 25%, and preferably will be less than 10%, even after ambient to relatively high temperature storage, for example, at 20° to 40° C., for periods of time of several weeks up to a year or more. It is considered that the most stable dentifrices are those which include a stabilizing proportion of terpene or other suitable stabilizer and also include contacting container parts of polyfluoroethylene (and/or any of the other "unreactive" plastics) only. Although the terpenes and essential oils are the primary stabilizers utilizable in accordance with the present invention, other flavor components may also contribute to the stabilization of the antiplaque material by interfering with any destabilizing chemical reaction or by inhibiting absorption of the triclosan by the plastic (or by other mechanism). It has been proposed that some components of dentifrices that tend to solubilize triclosan can act to maintain it in the dentifrice and inhibit or prevent its migration into the plastic but, on the other hand, it has also been theorized that such a solubilizing action could promote migration of the solubilized triclosan into the plastic. Because the issue has not been resolved applicants should not be considered to be bound by either theory. Also, while it is desirable for the terpenes and other stabilizers to be flavor components, that is not necessary, and the stabilizer may be useful solely for its stabilization function.

Although it is preferred that the packages of this invention should include internal surfaces, liners and other parts which come into contact with the packaged dentifrices that are of or are lined with synthetic organic polymeric plastic material, it is within the invention to utilize other solid (and/or film-forming) polymeric materials, whether or not they are synthetic, organic or even plastic. Thus, polyethylene glycols and methoxypolyethylene glycols, such as those of the Carbowax ® type, e.g., Carbowax 4,000 and Carbowax 6,000, may sometimes be employed as coatings or lining materials for parts of the present dispensers. Well known silicon polymers, such as siloxanes, and natural organic film-forming materials, such as gums, e.g., carrageenan, tragacanth, karaya, may also be useful for such purposes, as may be other solid polymeric materials, such as cellulose, starches and derivatives thereof.

The dentifrices of this invention are comprised of three classes of components, vehicle, polishing material and surfactant (or detergent). Triclosan is normally present in the vehicle of the packaged dentifrices, which vehicle usually comprises about 10 to 80%, preferably 50 to 80% (the figures are on a final composition basis) of the dentifrice. Of the vehicle, about 20 to 90%, preferably 30 to 80%, will be water, about 20 to 80%, preferably 30 to 60%, will be humectant, such as glycerol, sorbitol, propylene glycol, polyethylene glycol or any suitable mixture thereof, and 0.5 to 10%, preferably 1 to 5%, will be gelling agent, such as sodium carboxymethyl cellulose, Irish moss, iota carrageenan calcium carrageenan, or hydroxyethyl cellulose or the like, including any suitable mixtures thereof. Although triclosan is essentially insoluble in water it is soluble or at least readily dispersible in the described dentifrice vehicle. The polishing material of the dentifrice will normally be from about 10 to 50%, preferably 15 to 25% thereof and such polishing material may be colloidal silica, precipitated silica, hydrated silica, sodium aluminosilicate, insoluble sodium metaphosphate, hydrated alumina, calcined alumina, dicalcium phosphate dihydrate, anhydrous dicalcium phosphate or calcium carbonate, or other known polishing agent, or any suitable mixture thereof. The surfactants include anionic, nonionic, cationic and zwitterionic surfactants but often the employment of nonionic surfactant is avoided in the packaged dentifrices of this invention because of its adverse affect on triclosan, and the employments of cationic and zwitterionic surfactants are also often avoided because they tend to stain or darken the teeth. Thus, synthetic organic anionic surfactants, which are also detergents, are the preferred cleaning agents in the present dentifrices and of these, sodium lauryl sulfate and other sodium higher alkyl sulfates of 10 to 18 carbon atoms in the alkyl groups thereof, and ethoxylated such sulfates, of 1 to 15 ethoxy groups per mole, are preferred, although various other well known sulfated, ethoxysulfated and sulfonated detergents, preferably of similar carbon chain lengths, may be substituted for them, at least in part. The surfactant or detergent content, usually anionic detergent content, is normally in the range of 0.2 to 10%, preferably 0.5 to 5%, and more preferably 1 to 3%.

In the packaged dentifrices of this invention there will very preferably also be present an effective anti-tartar (and anti-calculus) proportion of polyphosphate. Representative examples of suitable polyphosphates, for the purpose of this description, include metaphosphates, such as sodium hexametaphosphate, polyphosphates, such as sodium tripolyphosphate, and pyrophosphates, such as tetrasodium pyrophosphate (which is more preferred), disodium diacid pyrophosphate and trisodium monoacid pyrophosphate, the corresponding potassium salts, and the like. Such polyphosphates also include the linear molecularly dehydrated polyphosphate salts which are generally employed in the forms of their wholly or partially neutralized water soluble alkali metal (e.g., potassium and preferably sodium) or ammonium salts, and any mixtures thereof. Linear polyphosphates are includable as anti-tartar agents. In the present invention the polyphosphates are present in the dentifrices in concentrations of 0.1 to 3%, preferably 0.5 to 3% and more preferably 1.5 to 2.5%, e.g., about 2%. Particularly desirable are tetraalkali metal pyrophosphates, including mixtures thereof, such as tetrasodium pyrophosphate, tetrapotassium pyrophosphate and mixtures thereof.

To improve the anti-calculus and anti-tartar effectiveness of the oral composition an inhibitor against enzymatic hydrolysis of the polyphosphate is desirably present. Such an agent is a fluorine ion source sufficient to supply 25 p.p.m. to 5,000 p.p.m., preferably 500 to 3,000 p.p.m. of fluorine ions (or fluoride ions) in the dentifrice.

Sources of fluorine ions or fluorine ion-providing components for inhibiting the actions of acid phosphatase and pyrophosphatase enzymes on polyphosphate (and thereby for increasing anti-tartar and anti-calculus effectiveness of the polyphosphate) in the present dentifrices are well known in the art, and usually also function as tooth hardeners and anti-caries agents. These compounds may be slightly soluble in water or may be fully water soluble. They are characterized by their ability to release fluorine (or fluoride) ions in water and by their relative inertness toward other components of the oral preparations. Among these material are inorganic fluoride salts, such as soluble alkali metal and alkaline earth metal salts, e.g., sodium fluoride, potassium fluoride, ammonium fluoride, zinc fluoride, barium fluoride, tin fluoride, sodium fluorosilicate, ammonium fluorisilicate, sodium fluorozirconate, ammonium fluorozirconate, sodium monofluorophosphate, aluminum mono- and difluorophosphates, and fluorinated sodium calcium pyrophosphate. Alkali metal and tin fluorides, such as sodium and stannous fluorides, sodium monofluorophosphate (MFP®) and mixtures thereof are preferred.

The amount of fluorine-providing compound in the present dentifrices is dependent to some extent upon the type of compound, its solubility, and the type of dentifrice, but it should be a non-toxic amount, generally in the range of about 0.005 to about 3.0% and preferably in the range of 0.05 to 1%, in the dentifrice.

Typically, in the cases of alkali metal fluorides, this component is present in an amount up to about 2% by weight, e.g., 0.05 to 2%, based on the weight of the preparation, and preferably in the range of about 0.1 to 1%, e.g., about 0.33% or 0.3%. In the case of sodium monofluorophosphate, the compound may be present in an amount of about 0.1 to 3%, typically 0.5 to 1%, e.g., about 0.76% or 0.8%.

In another preferred aspect of this invention the dentifrice comprises an agent that is effective to enhance the antibacterial and anti-plaque effect of the triclosan. Such antibacterial enhancing agent (AEA) is preferably of an average molecular weight in the range of about 1,000 to about 1,000,000 and desirably contains a functional group which enhances delivery of the antibacterial agent and an organic group which enhances retention of such antibacterial agent on treated surfaces.

The AEA is preferably a synthetic anionic polymeric polycarboxylate which is also an inhibitor of alkaline phosphatase enzyme. In U.S. Pat. No. 4,627,977 (Gaffar et al.) there is described the use of polycarboxylates for inhibiting salivary hydrolysis of pyrophosphate anticalculus agents in combination with a compound providing a source of fluoride ion. It is to be understood that the synthetic anionic polymeric polycarboxylates so disclosed, when containing or modified to contain the retention-enhancing group mentioned above, are operative as AEA's in the packaged compositions of this invention and are components of preferred embodiments thereof.

The mentioned synthetic anionic polymeric polycarboxylates may be employed in the forms of their free acids but preferably are partially and more preferably fully neutralized water soluble or water swellable (hydratable, gel/forming) alkali metal (e.g., potassium and preferably sodium) or ammonium salts. Preferred are 1:4 to 4:1 copolymers of maleic anhydride or equivalent acid with another polymerizable ethylenically unsaturated monomer, preferably methyl vinyl ether/male anhydride copolymers with a molecular weight (M.W.) of about 30,000 to about 1,000,000. These copolymers are available from GAF Corporation as, for example, Gantrez ® AN 139 (M.W. =500,000), Gantrez AN 119 (M.W. =250,000), and preferably Gantrez S-97 Pharmaceutical Grade (M.W. =70,000).

Other polymeric polycarboxylates which are operative as AEA's and contain or are modified to contain retention-enhancing groups include those disclosed in U.S. Pat. No. 3,956,480, such as the 1:1 copolymers of maleic anhydride with ethyl acrylate, hydroxyethyl methacrylate, N-vinyl-2-pyrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates are those disclosed in U.S. Pat. Nos. 4,138,477 and 4,183,914, which contain or may be modified to contain retention-enhancing groups. These include copolymers of maleic anhydride with styrene, isobutylene or ethyl vinyl ether, polyacrylic, polyitaconic and polymaleic acids, and sulfoacrylic oligomers of a M.W. as low as 1,000, available as Uniroyal ND-2.

Other suitable anionic polymers that may be employed as AEA's are described in greater detail in U.S. Pat. No. 3,956,480 and in Ser. No. 07/398,605, both of which are incorporated herein by reference. The percentage of such AEA(s) in the described compositions will normally be in the range of 0.2 to 5%, preferably being 0.5 to 4% and more preferably 1 to 3%, e.g., 2%.

In dentifrice compositions the effective amount of triclosan will normally be in the range of 0.1 to 1.0%, more preferably 0.2 to 0.5 or 0.6%, e.g., about 0.3%, and often not exceeding 0.8% because of possible mouth numbing effects at high concentrations, and not being less than indicated to avoid ineffectiveness against plaque when the dentifrice is brushed on the teeth in normal manner. Preferably the dispensed compositions will contain proportions of triclosan within the given ranges but when the initial concentration thereof is within the given range a loss of up to 25% will be acceptable and such dispensed compositions are effective in removing plaque.

For stabilized oral compositions that are to be packaged in dispensing containers containing plastic walls or other parts, contacting the dentifrice, when such plastics are those which are "reactive" with triclosan, 0.01 to 2% of terpene(s) or stabilizer(s) preferably 0.05 to 1% and more preferably 0.1 to 0.5% will be present in the dentifrice. Such stabilizers may be present in a suitable flavoring agent for the dentifrice, if desired (and it often is), and will normally be at least 5% of the flavor, preferably at least 10%, more preferably at least 25% and most preferably at least 50% thereof.

The various plastics that were previously described as the components of dispensing container parts have been described only briefly because it is considered that their chemical natures and degrees of polymerization are well known, so detailing thereof is unnecessary in this specification. If further details are wanted reference may be made to *Modern Plastics Encyclopedia*, which has been published on an annual basis by McGraw-Hill Inc., New York, N.Y.

The stabilizing terpenes, which term, for the purpose of this specification, includes terpene hydrocarbons and oxygenated derivatives thereof, include such compounds as dllimonene, menthol, ionone, diterpenes, polyterpenes and derivatives thereof, many of which are found in various essential oils and other flavors. In addition to being useful as stabilizers for triclosan they often contribute desirable flavors to the present oral compositions. Of the terpenes and their derivatives it is considered that limonene best balances these properties, although other terpenes, such as menthol and pinene, and including those which are not flavors, are also useful, as are other emulsifiable lipophilic essential oils and flavoring agents which contain stabilizing components.

For other details of formulations, components, adjuvants, manufacturings and uses, see the patents and applications previously mentioned in this specification, which are hereby incorporated by reference, as are text and periodical references.

Manufacture of the described dentifrices is by any of various standard techniques for producing such compositions. Referring to specific examples for simplicity, the triclosan is dispersed and/or dissolved in the vehicle portion of the dentifrice and the terpene is present in the flavoring agent. To make the dentifrice, the vehicle is prepared, containing glycerol, sorbitol, and/or propylene glycol, gelling agents, triclosan and suitable adjuvants (including Gantrez S-97), and the vehicle and aqueous anionic detergent (preferably sodium lauryl sulfate or a mixture thereof with sodium methyl cocoyl taurate) solution are mixed, followed by blending in of the polishing agent component, which may include the polyphosphate and fluoride. Finally, flavoring agent, including terpene, desirably dissolved in ethanol, is admixed and the pH is adjusted, as desired, usually to the range of 6 to 10, preferably 7 to 9, e.g., about 8.

In packaging of the dentifrice in the dispensing container it will be desirable to avoid contacting of the dentifrice with any parts made of co-polyester/polyether elastomer and it will also be desirable to avoid contacting of any compositions not containing stabilizing agent (such as terpene or flavor containing it) with plastic parts made of those plastics previously listed in this specification as reactive with triclosan and other such antibacterial and anti-plaque compounds. It will be especially important to avoid the mentioned plastic parts for holding tanks or any other containers, piping, pumps or equipment, in which the triclosan or the dentifrice containing it may be held for any appreciable length of time or held for shorter lengths of time at elevated temperatures.

Even when the packaged compositions of this invention are prepared and contacts of the dentifrices containing triclosan with the reactant plastics are avoided it will still be desirable to minimize exposures of such packaged dentifrices to heat and to light, both of which have been found to accelerate losses of anti-plaque activity. Thus, the invented compositions are preferably stored and packaged in opaque dispensers or ones that filter out actinic light, at a temperature in the range of 10° to 38° C. Otherwise, the packaged dentifrices may be stored and used in normal manner and the desirable anti-plaque and anti-tartar effects thereof will be obtained. Such effects have been verified by laboratory testing and by evaluations of the teeth of volunteers serving on human panels, who employed various packaged dentifrices and controls as directed. Significant improvements in anti-plaque activities of the compositions of this invention packaged in the described dispensers are obtainable compared to control dentifrices similarly packaged but wherein the dispenser includes plastic parts that are "reactive" with the triclosan and wherein the dentifrice does not contain any stabilizing agent. Such improvements are also found when dispensers made of "reactive" plastics (but not copolyester/polyether elastomers) are employed with dentifrices containing terpenes and are compared to controls in which the dentifrice contains no stabilizing terpenes and/or flavoring agents.

The following examples illustrate but do not limit the invention. Unless otherwise indicated, all percentages and proportions in these examples, the specification and the appended claims are by weight, and all temperatures are in °C.

EXAMPLE 1

| Component | Percent |
|---|---|
| Propylene glycol | 10.00 |
| Iota carrageenan | 0.75 |
| Sodium fluoride | 0.33 |
| Sorbitol (70% aqueous solution) | 30.00 |

-continued

| Component | Percent |
|---|---|
| Sodium saccharin | 0.30 |
| Titanium dioxide | 0.50 |
| Sodium hydroxide (50% aqueous solution) | 0.80 |
| +Luviform TM (35% aqueous solution) | 4.76 |
| ++Zeodent TM 113 | 20.00 |
| +++Sident TM 22S | 2.00 |
| Sodium lauryl sulfate (94% active) | 1.60 |
| *Flavor | 0.95 |
| **Triclosan | 0.30 |
| | 100.00 |

+35% Aqueous solution of polyvinyl methyl ether/maleic anhydride copolymer (BASF Corp.)
++Silica polishing agent (J.M. Huber Corp.)
+++Silica thickening agent (Degussa Co.)
*Contains at least 25% of terpenes, e.g., limonene
**Irgasan ® DP 300, mf'd. by CIBA-GEIGY A dentifrice of the above formulation is made in normal manner and is employed as a medium for testing the stability of triclosan when such dentifrice is exposed to different plastics which are employed as materials of dispensing containers or parts thereof in which or in contact with which such dentifrice is stored and dispensed. The plastics for the tests are Pibiflex TM 46, mf'd. by Inmont, and Arnitel TM 460 EM, mf'd. by AKZO, which are plastics that have previously been employed as the membrane or bellows of a pump dispenser, the so-called Guala dispenser, and which are also employable as parts of squeeze-type dispensers, such as that shown in the drawing. Six samples of plastics are tested, three of each of the mentioned plastics, with each of the three being treated with a different mold release agent (to determine whether the nature of the release agent is relevant to the problem of triclosan stability in contact with plastics during storage). The release agents are Silicone Master TM (5% silicone oil and 95% polypropylene), Silicone Master plus Silicone Oil (with extra silicone oil) and Armid O Master TM (5% oleyl amide and 95% polypropylene), respectively. After two weeks storage of the test samples in contact with the dentifrice at different temperatures (room temperature, 38° C. and 49° C.), the dentifrice samples are removed from the plastic container materials and the plastics are washed with water and immersed in methanol to dissolve any triclosan which might have been taken up by them during storage. The methanol washings are collected and are analyzed, using high performance liquid chromatography. It is found that essentially the same types of absorptions of triclosan take place with the different membrane materials and although there are variations between them and such are somewhat dependent on the release agents employed, the results are essentially the same in all cases. The co-polyester/polyether elastomers are found to absorb significant percentages of triclosan from the dentifrice (more than 25% of that which is present initially) which results are confirmable when the co-polyester/polyether elastomers are used as materials in dispenses containing the described dentifrice and other dentifrices within the invention. Accordingly, it is considered undesirable to employ co-polyester/polyether elastomers in contact with the present dentifrices and that is even so when the dentifrices contain terpenes or contain flavoring materials which include terpenes (which are present in the flavoring of the dentifrice formulation), to the extent of at least 0.1% of the dentifrice.

When the tests are repeated, using squeeze dispensers having bags or liners which are of Arnitel TM, as the co/polyester/polyether elastomer, losses of anti-plaque activity of triclosan are unacceptable but when the co-polyester/polyether elastomer is replaced by other less incompatible plastics, e.g., Teflon ® polyfluoroethylene, the triclosan activity is improved to within acceptable limits. Also, other plastic parts of such dispensers, such as polyethylene, polypropylene, nylon, polyethylene terephthalate and polymethyl methacrylate, do not absorb excessive amounts of triclosan and do not seriously decrease the anti-plaque activity of the dentifrice, apparently due to the presence of terpenes in the flavoring agent of the contained dentifrice.

A panel test is run, involving at least ten human subjects who employ the dentifrice of this example, dispensed from polyethylene terephthalate- and polyethylene-lined dispensing containers in twice-a-day brushings for one month, during which time plaque evaluations of the subjects' teeth are made by trained observers. The test results establish that the dentifrice composition has a definite anti-plaque activity and also prove that the triclosan has not been unacceptably inactivated, and still is present in an effective antibacterial and anti-plaque proportion in the dentifrice Similar good results are obtainable when squeeze dispensers like that illustrated in FIG's. 1-3 are employed and comprise parts of high and low density polyethylenes, polypropylenes, polyallomers, nylons, acrylics, polyethylene terephthalates, polymethyl methacrylates, polyfluorocarbons, polyvinyl halides, polycarbonates, and/or polysulfones. Such stability of the triclosan is also obtainable when the terpene content is decreased or when terpenes are omitted, providing that the plastic parts are of polytetrafluoroethylene, polyvinyl chloride, polycarbonate and/or polysulfone.

The dentifrice formula will desirably also include 1.5 to 2.5%, e.g., 2%, of a polyphosphate (sodium hexametaphosphate, tetrasodium pyrophosphate, or sodium tripolyphosphate, or a mixture thereof), preferably the pyrophosphate, to give the dentifrice desired anti-tartar action. It is also highly preferable for such compositions to contain a fluorine ion releasing compound, such as 0.3% of sodium fluoride or 0.8% of sodium fluorophosphate, and 2% of polyvinyl methyl ether/maleic anhydride copolymer, for their functions that were previously mentioned herein. The compositions resulting by such modifications of the basic formula are also effective as anti-plaque dentifrices despite storage in and dispensing from plastic squeeze dispensers that include materials previously indicated to be reactive with triclosan. Adding of the mentioned materials to the formula is compensated for by decreasing the water content accordingly.

EXAMPLE 2

| Component | Percent |
| --- | --- |
| Glycerol | 7.00 |
| Propylene glycol | 3.00 |
| Iota carrageenan | 0.75 |
| Sorbitol (70%) | 30.00 |
| Sodium saccharin | 0.30 |
| Sodium fluoride | 0.33 |
| Titanium dioxide | 0.50 |
| Gantrez S-97 (13% solution) | 15.00 |
| Deionized water | 16.07 |
| Sodium hydroxide (50% aqueous solution) | 0.80 |
| ***Zeodent 113 | 20.00 |
| °Sylodent ® 15 | 3.00 |
| Flavoring agent (containing at least 25% of terpenes) | 0.95 |

-continued

| Component | Percent |
| --- | --- |
| Sodium lauryl sulfate | 2.00 |
| Triclosan | 0.30 |
| | 100.00 |

***Polishing agent (J.M. Huber Corp.)
°Silica thickening agent (W.R. Grace Corp.)

A toothpaste of the above formula is made and is stored in squeeze dispensers of the type illustrated in the drawing, which include a laminate of 0.001 inch of polyethylene next to the dentifrice, 0.0001 inch of aluminum, 0.0005 inch of polyethylene terephthalate and 0.001 inch of polyethylene, as the material of construction of the bag or liner, and other of the satisfactory (with terpene stabilizer) plastics, e.g., polyethylene, polypropylene and polytetrafluoroethylene, for the other parts (passageway, orifice, check valve and suckback valve parts) that contact the dentifrice. The dentifrice is also filled into the dispensing containers and contacts the polyethylene of the laminated bag, after which the other upper parts are installed and the package is closed. The dentifrices are aged at 5° C., 25° C., and 39° C., for two, four and six weeks. After such aging periods, the dentifrices are dispensed at the rate of about 1.5 grams per day and at weekly intervals the triclosan contents of the dispensed dentifrice are determinable by analyses. Triclosan stability will be satisfactory and the dispensed composition will be effective as an anti-plaque dentifrice.

Incorporation of tetrasodium pyrophosphate, sodium tripolyphosphate or sodium hexametaphosphate, as in Example 1, (preferably 2% of the pyrophosphate) makes the dentifrice anti-tartar, as well as anti-plaque, and additions of fluorine ion supplying compounds and Gantrez, as in Example 1, also contribute their desired effects.

Gel dentifrice formulations in such dispensers behave similarly to toothpastes with respect to triclosan stability after storage and on dispensing.

In similar tests, using polyethylene terephthalate (PET) lined dispensing containers, bags or liners or laminates having PET films as the interior surface thereof, as parts of the dispensing containers, and having other container parts of polyethylene and/or polypropylene little loss (less than 5%) triclosan will result, indicating that the presence of the terpene(s) (0.1% or more of the composition), including limonene, in the flavoring agent or as the flavoring agent, can prevent loss of the triclosan or inactivation thereof. When polyfluoroethylene lined or surfaced bags and other parts are employed there will be little loss of triclosan, even when the flavoring agent is omitted from the dentifrice composition, and such is also the case when polyvinyl chloride is employed as a primary bag material in contact with the dentifrice and/or when polysulfone or polycarbonate is/are used for other package parts in contact with the dentifrice.

In the above formulas the polishing systems are siliceous rather than being based on alumina. When the polishing agents are changed to aluminas, the triclosan stability problems previously mentioned as having been noted with some plastics are decreased, but they still exist. Also, the presence of terpenes in the dentifrices promotes triclosan stability in the presences of the "reactive plastics", as such terpenes do in similar dentifrice packages wherein the compositions are based on siliceous polishing agents.

EXAMPLE 3

The dentifrices of the foregoing examples may be varied in composition ±10% and ±25% for various components thereof, providing that such percentages are not outside ranges given elsewhere in this specification, and operative and effective anti-plaque products are obtainable, which are dispensable in effective anti-plaque state from the mentioned dispensing containers that are made of compatible plastics. Such products will also behave in similar manners, with the triclosan anti-plaque agent being sufficiently stable in the presence of polyfluoroethylene, polyvinyl chloride, polycarbonate and polysulfone packaging or package component materials, even when no flavoring agent and no terpenes are present in the dentifrices, and being stable in the presence of polyethylenes, polypropylenes, polyethylene terephthalates, polyesters, polyethers, polymethyl methacrylates, polyacrylates, polyallomers, nylons and polymethyl pentenes, as package or component materials, when a stabilizing terpene, such as limonene, or a stabilizing flavor component is present in the dentifrice. The packaged dentifrices of this example that contain polyphosphate, source of fluorine ions and AEA are also of effective anti-tartar, anti-calculus, anti-caries, tooth hardening and stabilizing (of the polyphosphate against enzymatic action) properties. When the AEA materials and fluoride are omitted the polyphosphate's anti-tartar and anti-calculi properties can be adversely affected by enzymatic action of the saliva but some will be present. As with the other packaged dentifrices previously discussed, because of excessive absorption or other adverse action with respect to triclosan by copolyester/polyether and other such elastomers, uses of such materials will preferably be avoided.

In addition to changing the dentifrice formula, other changes may be made in the dispensing container. Thus, it is not necessary for the container to incorporate a suckback limiting valve for the dentifrice to be effective in fighting plaque. Sometimes the absence of such a valve may be compensated for by utilizing an air venting mechanism (at the container "bottom") which is larger and more readily able to vent air back into the container, thereby decreasing any suction applied to the dentifrice that had been partially discharged, as squeezing forces are removed. Also, one can employ a more viscous dentifrice or smaller opening(s) in part 25. Alternatively the user could release squeezing forces more gradually.

Dentifrices of the formulas of Examples 1 and 2 are made and are dispensed after one month's storage at 30° C., from containers lined with polyethylene, in one case, and polyethylene terephthalate, in another, onto bristled toothbrushes. The amounts of toothpaste on the toothbrushes are in the range of 0.8 to 2.0 grams with 1 to 1.5 g. being preferred. When 1.5 g. is dispensed the active triclosan in the dentifrice on the brush will be about four milligrams (with only 10% of the triclosan being inactivated). When storage is for a longer time or at a higher temperature or with a more destabilizing plastic in contact with the dentifrice during storage and dispensing the content of triclosan in the composition can be increased so that the dispensed composition will contain about 3.5 or 4 mg. of triclosan in the 1.5 g. of dentifrice on the brush.

The described dispensed dentifrices are employed to brush the teeth, with typically about 0.8 to 2 g. being dispensed onto toothbrushes for each brushing. Brushings are twice a day, morning and night, one minute at a time, for four weeks, after which definite improvement in anti-plaque action will be apparent, compared to similarly stored and dispensed control dentifrice that contains no triclosan, and when polyphosphate is also present, especially with a source of fluorine ion and an AEA, anti-tartar effects are also noticeable. Improvement in anti-plaque action is also obtainable compared to an unflavored control (containing no terpene) that contains triclosan which is dispensed from polyethylene and polyethylene terephthalate lined containers.

For more details about the dispensers, materials of construction thereof and dentifrice composition components of the invention, if desired, please see the previously mentioned or referred to patents, applications, texts, bulletins and/or articles, which are hereby incorporated herein by reference.

The invention has been described with respect to various examples, illustrations and embodiments thereof but is not to be limited to these because it is evident that one of skill in the art, with the present specification before him/her, will be able to utilize substitutes and equivalents without departing from the invention.

What is claimed is:

1. An article comprising a viscous anti-plaque, anti-tartar dentifrice comprising 0.1 to 1% of triclosan, 0.1 to 3% of polyphosphate and 0.01 to 2% of a stabilizing terpene which stabilizes the triclosan in the presence of synthetic organic polymeric plastic container parts, in a form-maintaining resilient squeezable dispensing container which has a walled dispensing chamber, in which container parts thereof that contact the dentifrice during storage and during dispensing thereof comprise polyethylene terephthalates, poly-lower alkylenes or pluralities thereof.

2. An article comprising a form-maintaining resilient squeezable dispensing container having solid destabilizing polyethylene or polyethylene terephthalate polymeric material in contact with a viscous anti-plaque, anti-tartar dentifrice in the dispenser, which dentifrice comprises an effective anti-plaque proportion of a halogenated diphenyl ether and a stabilizing proportion of a terpene which stabilizes the halogenated diphenyl ether in the presence of said destabilizing material.

3. An article according to claim 2 wherein said destabilizing material comprises polyethylene, said halogenated diphenyl ether comprises triclosan and said terpene comprises limonene.

4. An article comprising a hand holdable resilient squeezable form-maintaining dispensing container having solid polyethylene or polyethylene terephthalate polymeric material in contact with a dentifrice composition in the container, which composition comprises an effective antibacterial antiplaque proportion of a substantially water insoluble non-cationic halogenated diphenylether antibacterial antiplaque agent, at least about 25% of which has been found to be lost after twelve weeks storage at room temperature in said container, and a stabilizing terpene to make said polymeric material compatible with said agent in the presence of the oral composition whereby said loss is prevented and the dispensed composition contains more than about 75% of its initial content of said agent.

5. An article according to claim 4 wherein the stabilizing terpene is not a component of a flavoring agent.

6. An article according to claim 1 wherein the stabilizing terpene is not a component of a flavoring agent.

7. An article according to claim 4 wherein the dentifrice is in paste or gel form.

8. An article according to claim 4 in which the dentifrice comprises 0.1 to 1% of triclosan.

9. An article according to claim 4 in which the dentifrice comprises an effective anti-tartar proportion of synthetic linear molecularly dehydrated polyphosphate antitartar agent.

10. An article according to claim 9 in which the dentifrice comprises 0.1 to 3% of said polyphosphate antitartar agent.

11. An article according to claim 4 in which the dentifrice comprises an effective proportion of an antibacterial enhancing agent (AEA) which comprises a synthetic anionic polymeric polycarboxylate.

12. An article according to claim 11 wherein the AEA comprises methyl vinyl ether/maleic anhydride copolymer of average molecular weight in the range of 1,000 to 1,000,000.

13. An article according to claim 4 in which the dentifrice comprises an effective proportion of a source of fluorine ion sufficient to stabilize the polyphosphate against enzymatic hydrolysis.

14. An article according to claim 13 wherein the source of fluorine ion comprises 0.005 to 3% of an inorganic fluoride or monofluorophosphate.

15. An article according to claim 4 in which the dentifrice is an aqueous paste or gel or mixture thereof, which comprises a vehicle, a polishing gent, a surfactant and triclosan, and the container comprises a walled resilient tube, a flexible bag or liner, a bottom for such tube, an air check valve to prevent passage of air out from between the bag and the tube, near the bottom thereof, during squeezing of the package, and to permit entrance of air during resilient return of the tube to normal shape after release of squeezing forces, a dispensing passageway and an outlet, with the passageway communicating the dentifrice in the bag or liner with the outlet, and dentifrice suckback limiting means between the dispensing outlet and the flexible bag, which limit entry of air into the dispensing container through the outlet and thereby prevent belching of air from the dispensing container during use thereof.

16. An article according to claim 15 in which the dentifrice comprises 0.2 to 0.8% of triclosan, 0.5 to 3% of polyphosphate antitartar agent, 0.005 to 3% of a source of fluorine ions and 0.2 to 5% of synthetic anionic polymeric polycarboxylate, and in the squeezable dispensing container the portion of the bag or liner that contacts the dentifrice comprises polyethylene.

17. An article according to claim 16 wherein the bag or liner is a laminate which includes a non-contacting barrier layer of metal.

18. An article according to claim 4 in which the dentifrice comprises 0.01 to 2% of stabilizing terpene(s).

19. An article according to claim 4 in which the dentifrice is an aqueous paste or gel or mixture thereof, which comprises a vehicle, a polishing agent, a surfactant and triclosan, and the container comprises a walled resilient tube, a flexible bag or liner, a bottom for such tube, an air check valve to prevent passage of air out from between the bag and the tube, near the bottom thereof, during squeezing of the tube, and to permit entrance of air during resilient return of the tube to normal shape after release of squeezing forces, a dispensing passageway and an outlet, with the passageway communicating the dentifrice int he bag or liner with the outlet, and dentifrice suckback limiting means between the dispensing outlet and the flexible bag, which limit entry of air into the dispensing container through the outlet and thereby prevent belching of air from the dispensing container during use thereof.

20. An article according to claim 19 wherein the dentifrice comprises 0.1 to 1% of triclosan.

21. An article according to claim 19 wherein the dentifrice comprises 0.1 to 3% of synthetic linear molecularly dehydrated polyphosphate.

22. An article according to claim 19 wherein the dentifrice comprises 0.05 to 1% of a source of fluorine ions.

23. An article according to claim 19 wherein the dentifrice comprises 0.2 to 5% of synthetic anionic polymeric polycarboxylate.

24. An article according to claim 19 wherein the dentifrice comprises 0.1 to 1% of triclosan, 0.1 to 3% tetrasodium pyrophosphate, sodium tripolyphosphate or sodium hexametaphosphate or any mixture thereof, 0.05 to 1% of sodium fluoride or sodium monofluorophosphate or a mixture thereof, 0.2 to 5% of polyvinyl methyl ether/maleic anhydride copolymer, and 0.05 to 1% of stabilizing terpene(s).

25. An article according to claim 24 wherein the portion of the bag or liner that contacts the dentifrice comprises polyethylene.

26. An article according to claim 25 wherein the bag or liner comprises a laminate of polyethylene and polyethylene terephthalate.

27. An article according to claim 26 wherein the bag or liner laminate has an aluminum coating between polyethylene and polyethylene terephthalate laminate.

* * * * *